United States Patent
Zhang et al.

(10) Patent No.: US 8,355,550 B2
(45) Date of Patent: Jan. 15, 2013

(54) METHODS AND APPARATUS FOR VIRTUAL CORONARY MAPPING

(75) Inventors: Wei Zhang, Plainsboro, NJ (US); Ying Zhu, Monmouth Junction, NJ (US); Adrian Barbu, Tallahassee, FL (US); Richard Socher, Dresden (DE); Stefan Böhm, Oberasbach (DE); Peter Durlak, Erlangen (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1294 days.

(21) Appl. No.: 12/150,816

(22) Filed: May 1, 2008

(65) Prior Publication Data

US 2008/0275335 A1    Nov. 6, 2008

Related U.S. Application Data

(60) Provisional application No. 60/915,190, filed on May 1, 2007.

(51) Int. Cl.
*G06K 9/00* (2006.01)

(52) U.S. Cl. .............. 382/128; 128/922; 378/4

(58) Field of Classification Search .......... 382/100, 382/128, 130, 131, 132; 128/922; 378/4–27, 378/42–50; 600/309, 310, 317, 322, 329, 600/433–435
See application file for complete search history.

(56) References Cited

U.S. PATENT DOCUMENTS

| | | | | |
|---|---|---|---|---|
| 6,493,575 B1 * | 12/2002 | Kesten et al. | ........... | 600/431 |
| 6,532,380 B1 * | 3/2003 | Close et al. | ........... | 600/431 |
| 7,286,866 B2 * | 10/2007 | Okerlund et al. | ........... | 600/407 |
| 7,766,961 B2 * | 8/2010 | Patel et al. | ........... | 623/1.35 |
| 7,778,685 B2 * | 8/2010 | Evron et al. | ........... | 600/424 |
| 7,792,342 B2 * | 9/2010 | Barbu et al. | ........... | 382/128 |
| 2006/0247520 A1 * | 11/2006 | McGee | ........... | 600/434 |

FOREIGN PATENT DOCUMENTS

WO    WO 2006103644 A1 *    10/2006

OTHER PUBLICATIONS

Barbu Adrian, et al., "Hierarchical Learning of Curves Application to Guidewire Localization in Fluoroscopy", CVPR 2007.

* cited by examiner

*Primary Examiner* — Anand Bhatnagar

(57) ABSTRACT

A virtual map of vessels of interest in medical procedures, such as coronary angioplasty is created so that doses of contrasting agent given to a patient may be reduced. A position of a coronary guidewire is determined and locations of vessel boundaries are found. When the contrast agent has dissipated, virtual maps of the vessels are created as new images. The locations of the determined vessel boundaries are imported to a mapping system and an image obtained without using a contrast agent is modified based on the imported locations of vessel boundaries. This creates a virtual map of the vessels.

17 Claims, 16 Drawing Sheets

METHODS AND APPARATUS FOR VIRTUAL CORONARY MAPPING

This application claims the benefit of U.S. Provisional Application No. 60/915,190 filed May 1, 2007, which is incorporated herein by reference.

BACKGROUND OF THE INVENTION

The present invention relates generally to fluoroscopy and more particularly to virtual coronary mapping in fluoroscopy.

Coronary angioplasty is a medical procedure used to restore blood flow through clogged coronary arteries. During a coronary angioplasty procedure, a catheter containing a guidewire is inserted through an artery in the thigh and guided by a cardiologist until it reaches a blocked coronary artery. The catheter is stopped before a stenosis while the thin guidewire is guided through the stenosis. Then, a catheter with a deflated balloon is inserted along the guidewire and guided so that the balloon reaches the blockage. At that point, the balloon is inflated and deflated several times to unblock the artery and a stent is placed at that position to keep the artery from blocking again.

The procedure is monitored using real-time fluoroscopic images. A contrast agent is inserted into the patient periodically to aid in visualization of the navigation of the catheter, guidewire, balloon, and stent in the coronary tree. Generally, contrast agents have numerous safety concerns, including increasing the absorbed radiation rate in the tissue.

Therefore, methods and apparatus are required to reduce the quantity of contrast agent used during coronary angioplasties.

BRIEF SUMMARY OF THE INVENTION

The present invention provides methods and apparatus for coronary mapping in fluoroscopy.

A virtual map of vessels of interest in medical procedures, such as coronary angioplasties, is created so that doses of contrasting agent given to a patient may be reduced. A position of a coronary guidewire is determined and a reference system relative to the coronary guidewire is determined. Locations of vessel boundaries relative to the determined reference system are found. In some embodiments, the reference system is a relative coordinate system with a first dimension that is a length along the coronary guidewire relative to a catheter and a second dimension that is a distance between the coronary guidewire and a vessel boundary.

When the contrast agent has dissipated, virtual maps of the vessels are created as new images (e.g., frames). The locations of the determined vessel boundaries are imported to a mapping system and an image obtained without using a contrast agent is modified based on the imported locations of vessel boundaries. This creates a virtual map of the vessels.

These and other advantages of the invention will be apparent to those of ordinary skill in the art by reference to the following detailed description and the accompanying drawings.

DETAILED DESCRIPTION

The present invention generally provides methods and apparatus for coronary mapping in fluoroscopy.

Figure 1:
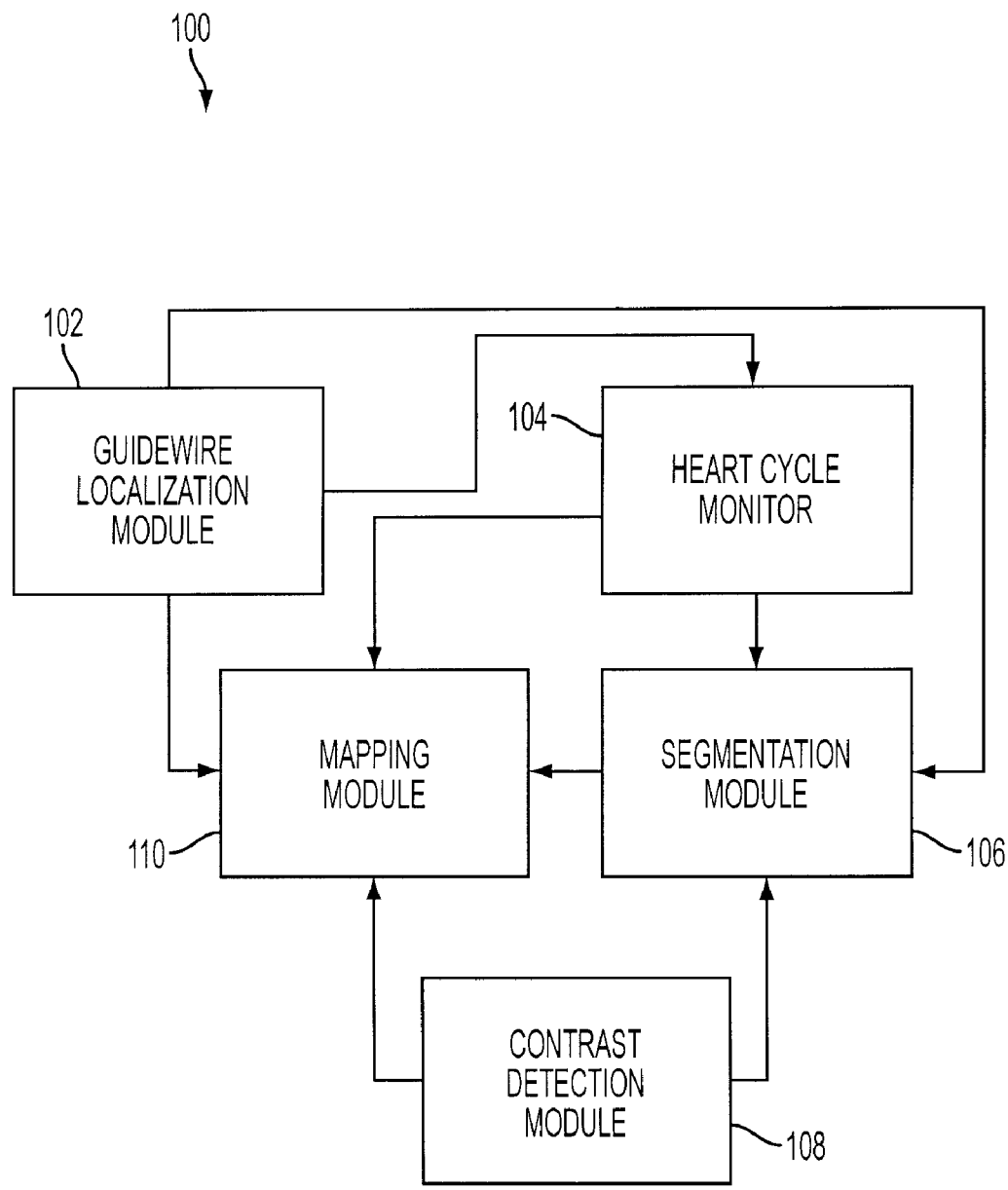
FIG. 1 depicts a coronary mapping system according to an embodiment of the present invention.

FIG. 1 depicts a coronary mapping system 100 according to an embodiment of the present invention. Coronary mapping system 100 comprises a guidewire localization module 102, a heart cycle monitor 104, a vessel segmentation module 106, a contrast detection module 108, and a mapping module 110. Coronary mapping system 100 may be implemented as part of a fluoroscopic imaging computer, such as computer 800, described below with respect to FIG. 8. In alternative embodiments, one or more of guidewire localization module 102, heart cycle monitor 104, segmentation module 106, contrast detection module 108, and mapping module 110 may be implemented as a stand-alone processor and/or computer capable of performing its attendant functions. The specific functions of guidewire localization module 102, heart cycle monitor 104, segmentation module 106, contrast detection module 108, and mapping module 110 are discussed in further detail below with respect to FIGS. 2-7.

Figure 2:
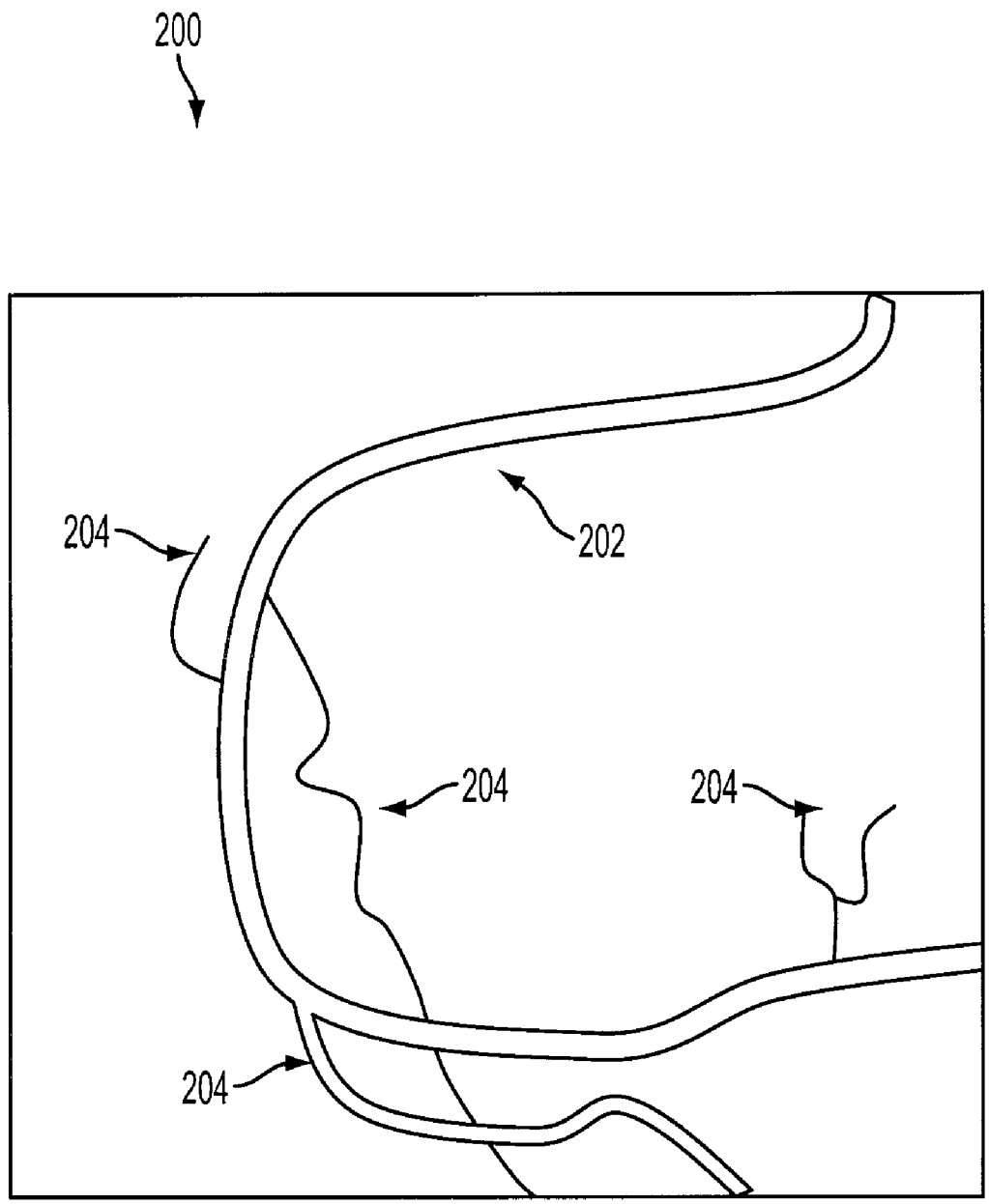
FIG. 2 depicts a representation of a contrast enhanced image of a vessel.

FIG. 2 depicts a contrast-enhanced image 200 of a vessel 202. Contrast enhanced image 200 represents a fluoroscopic image taken of a portion of a patient that has been injected with a radiocontrast agent as is known. Contrast enhanced image 200 shows the vessel 202 of primary interest as well as adjacent coronaries (e.g., coronary vessels, etc.) 204 and may be obtained through any appropriate imaging technique, such as in response to detection of a contrast agent by contrast detection module 108 of FIG. 1.

Figure 3:
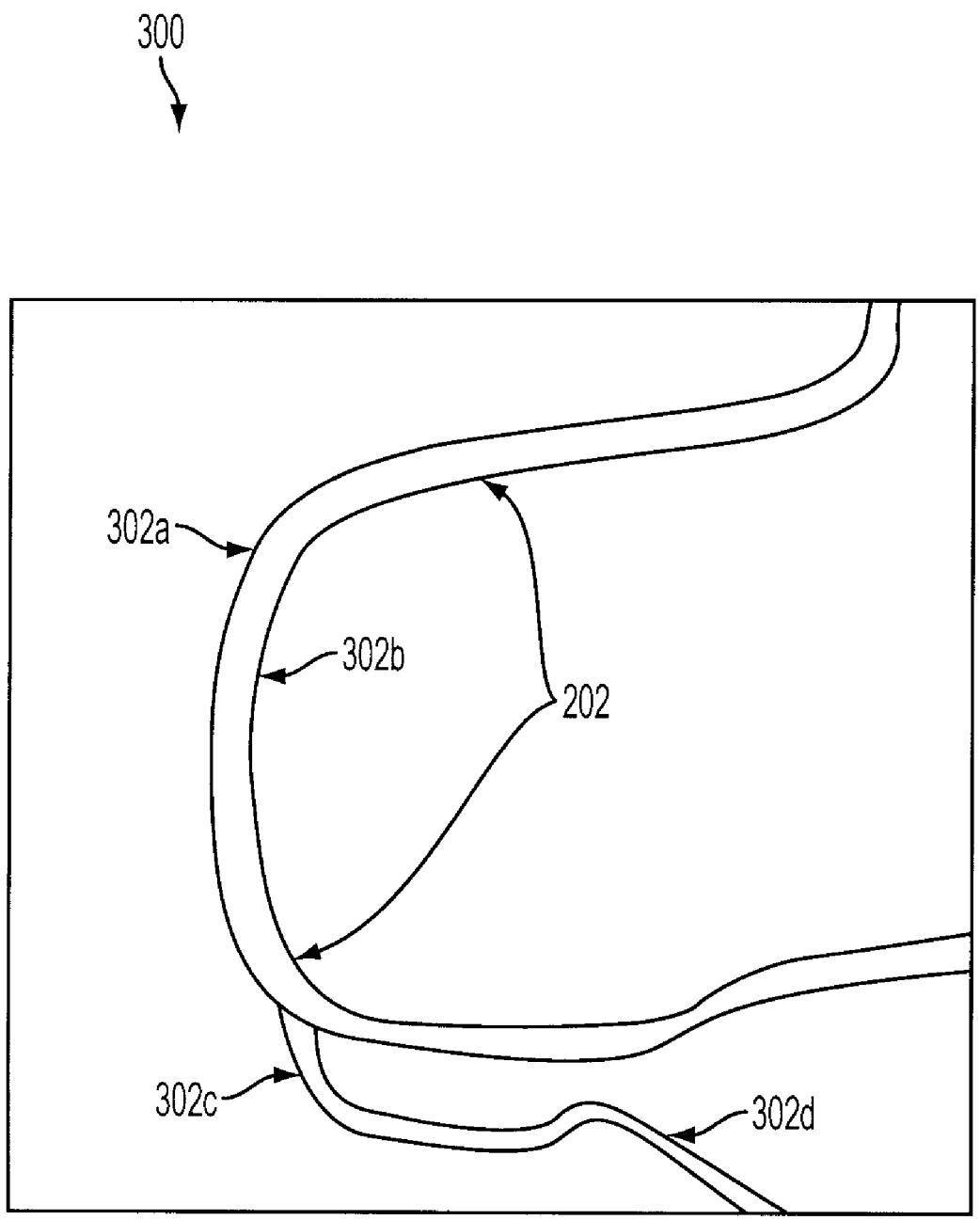
FIG. 3 depicts a representation of a segmented image of a vessel.

FIG. 3 depicts a segmented image 300 of vessel 202. Segmented image 200 is an image delineating the boundaries 302a, 302b, 302c, 302d and/or a centerline (e.g., a mid-point or approximate mid-point between boundaries 302a-d) of vessels in a contrasted image (e.g., contrast enhanced image 200). Segmented image 300 may be obtained by any appropriate segmentation method, such as those described in co-pending U.S. patent application Ser. No. 12/012,385, filed Feb. 1, 2008, the contents of which is incorporated herein by reference. Segmented image 300 may be obtained using spatial-temporal vessel segmentation by vessel segmentation module 106 of FIG. 1.

Figure 4:
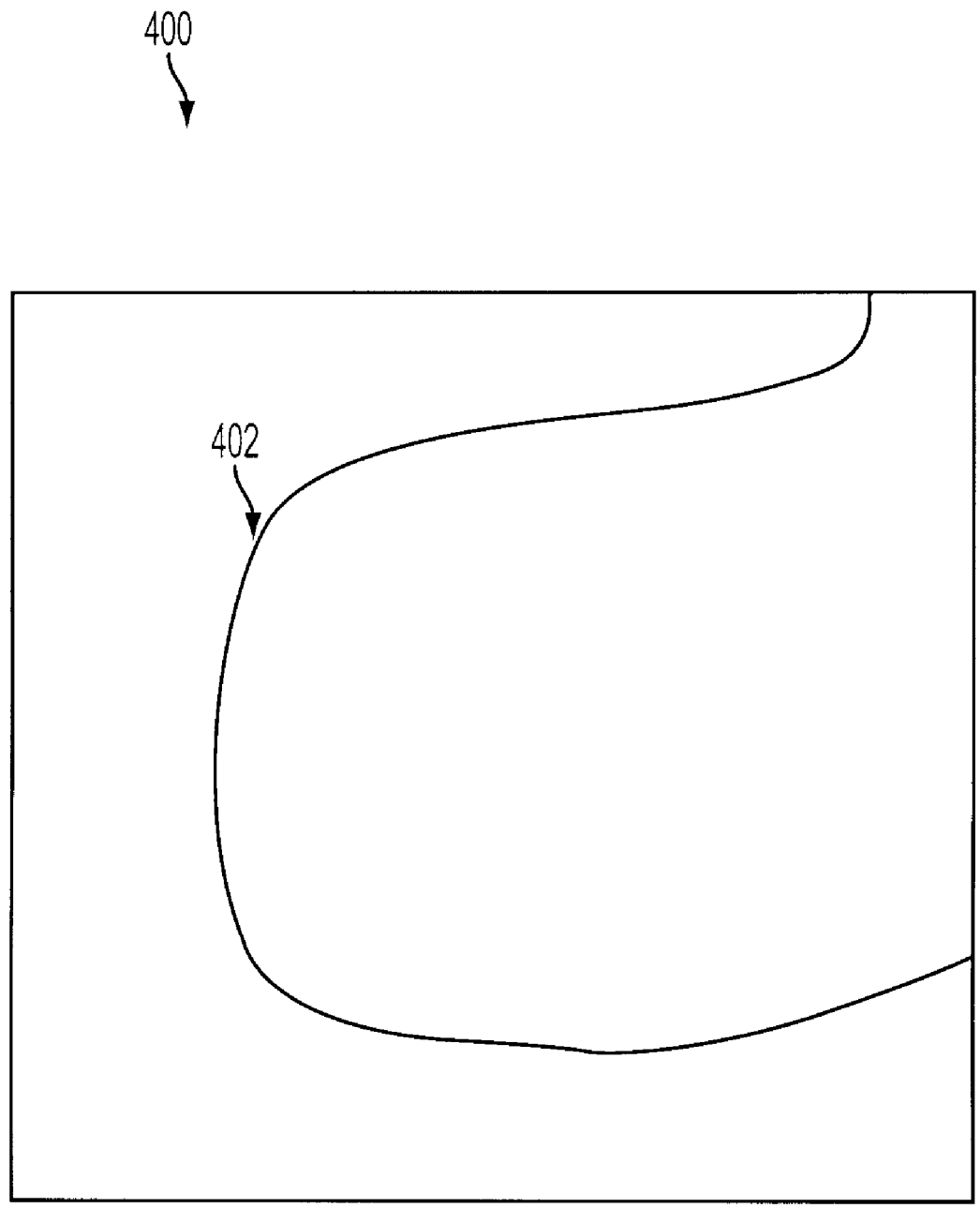
FIG. 4 depicts a representation of an image of a localized guidewire.

FIG. 4 depicts a representation of an image 400 of a localized (e.g., detected and tracked) guidewire 402. Guidewire 402 may be a guidewire for use in coronary angioplasty, as described above. The location of guidewire 402 (e.g., an image of localized guidewire 402) may be obtained by guidewire localization module 102 of FIG. 1. That is, localization module 102 may determine an image and/or coordinate and track information of the location of the guidewire 402 using any appropriate method.

Figure 5:
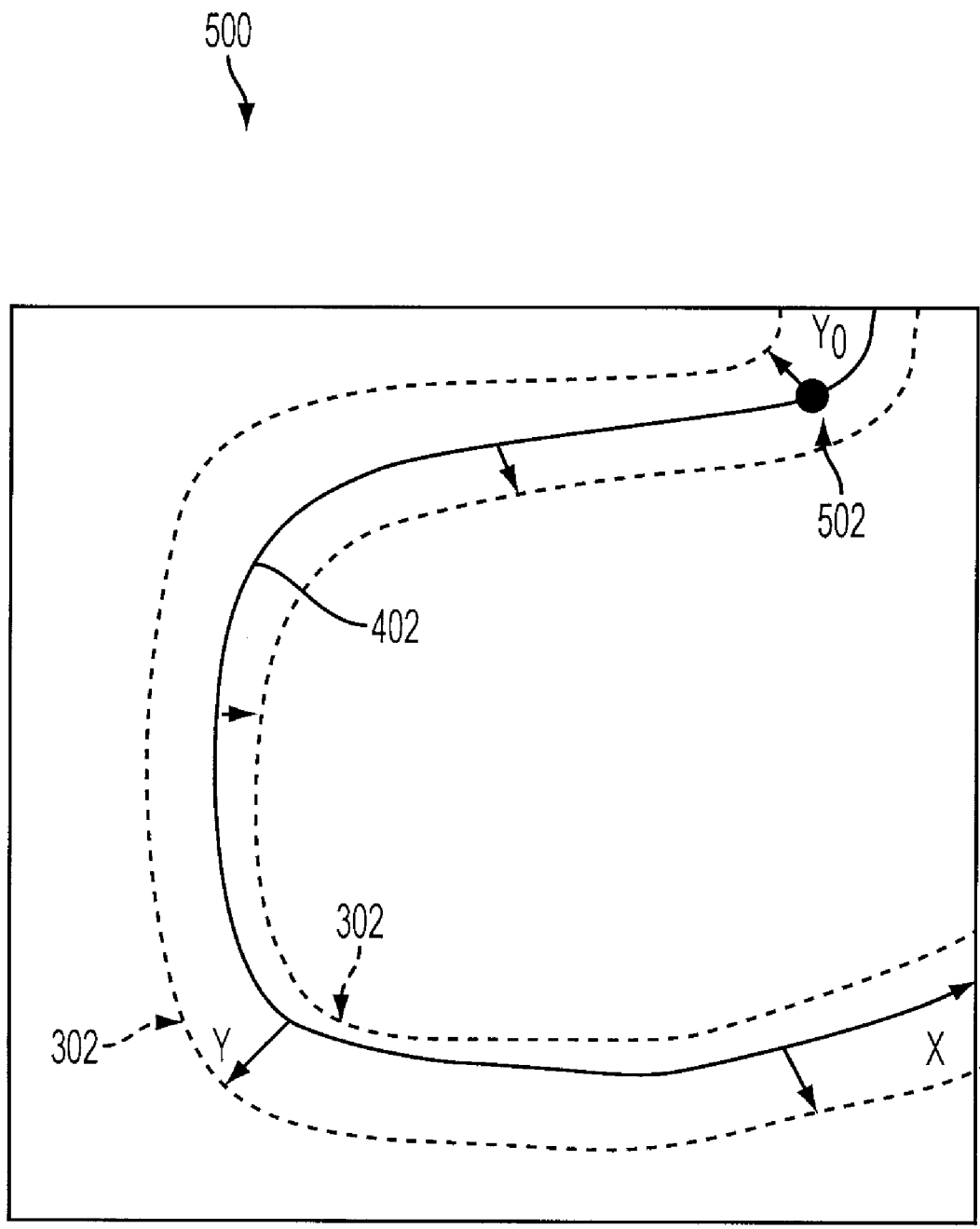
FIG. 5 depicts a representation of a reference system according to an embodiment of the present invention.

FIG. 5 depicts a reference system 500 according to an embodiment of the present invention. Reference system 500 may be a relative coordinate system determined relative to a guidewire (e.g., localized guidewire 402 of FIG. 4). Reference system 500 may be determined by guidewire localization module 102, segmentation module 106, and/or mapping module 110 of mapping system 100.

The coordinate system has a starting reference point 502, indicating the beginning of a first dimension of the relative coordinate system. The reference point 502 may, in some embodiments, be a location of a catheter disposed along guidewire 402. In this way, the reference system 500 is based on the current location of the catheter (e.g., at reference point 502) and the length of the guidewire 402, which may be expressed as the first, or X, dimension of reference system 500. Of course, other reference points 502 may be used as appropriate.

Reference system 500 also has a second dimension Y, which is the distance between guidewire 402 and the vessel boundaries 302, as described above with respect to FIG. 3. In at least one embodiment, Y is a second dimension defined locally, which is orthogonal to a local guidewire segment. For example, a distance $Y_0$, which is a distance from the origin to the vessel boundary 302, may be determined. Other distances in the Y dimension along the X dimension may be determined as appropriate to fully describe and/or create an image indicative of the vessel of interest (e.g., vessel 202, etc.).

Figure 6:
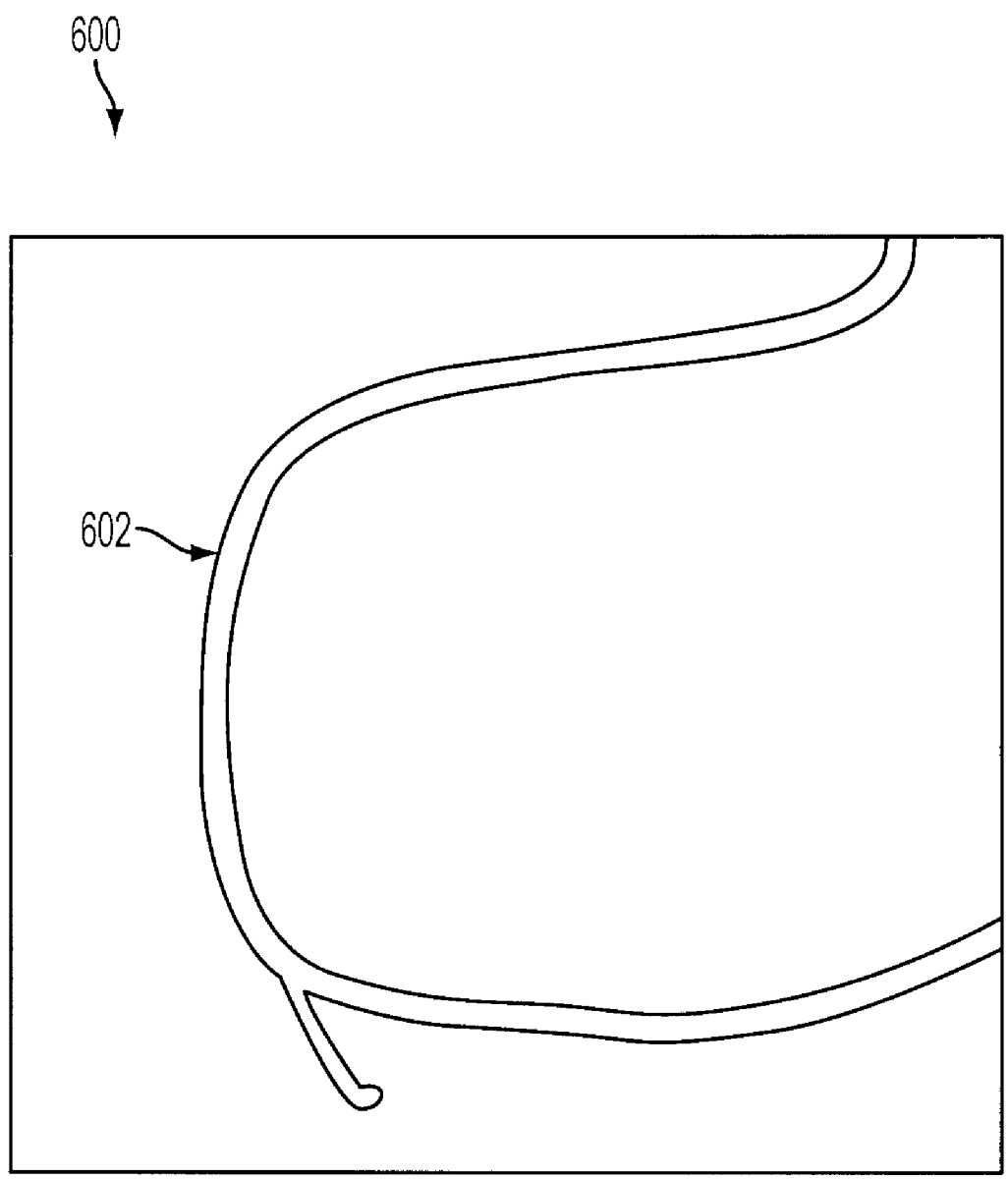
FIG. 6 depicts a representation of an image of a mapped contrast-free frame.

FIG. 6 depicts a representation of an image 600 of a mapped contrast-free frame. Image 600 may be obtained using mapping system 100, specifically mapping module 110 of FIG. 1. Creating the mapped contrast-free frame image 600 is described below with respect to method 700 of FIG. 7.

In at least one embodiment, image 600 is a virtual map 602 of vessel 202 that may be used in coronary angiography after a contrast agent has been absorbed by the patient. That is, before the contrast agent has worn away, the mapping system 100 creates a map of vessel 202 and/or any other appropriate vessels that may be later used by medical personnel to facilitate guidance of guidewire 402. This may reduce the amount of contrast agent a patient is exposed to since the medical personnel will have a "virtual map" of the vessels to refer to. In at least one embodiment, multiple mapped contrast-free frame images 600 are created. In these embodiments, each image 600 corresponds to a portion of a heart cycle as will be discussed in further detail below with respect to method 700 of FIG. 7.

Figure 7:
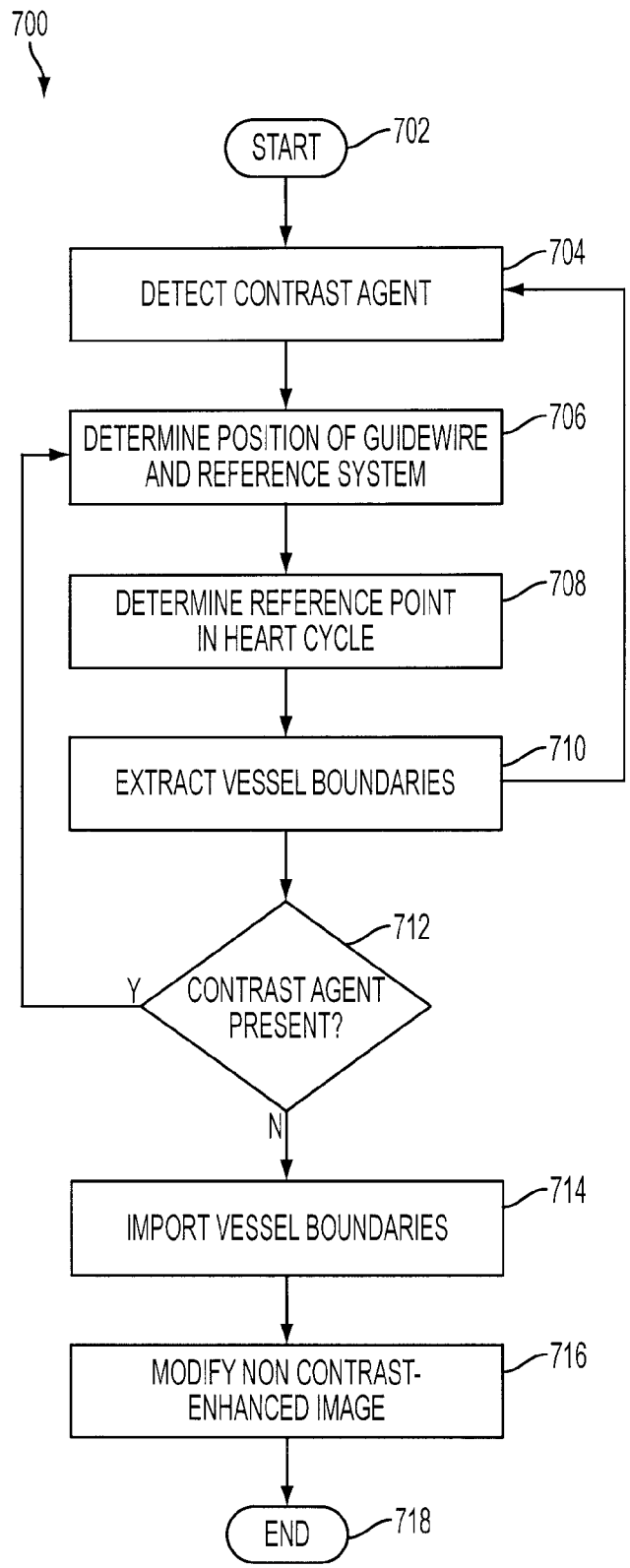
FIG. 7 depicts a flowchart of a method of mapping vessels in medical environments according to an embodiment of the present invention.

FIG. 7 depicts a flowchart of a method 700 of mapping vessels in medical environments according to an embodiment of the present invention. Method 700 may be performed by mapping system 100 as described above and may produce and/or use images 200-600, as will be described below. The method 700 begins at step 702.

In step 704, a contrast agent is detected. The presence of a contrast agent in a patient is detected by contrast detection module 108, which alerts segmentation module 106 and/or mapping module 110 to the presence of the contrast agent. In some embodiments, the contrast detection module 108 may receive contrast agent presence information from another outside source.

In step 706, a position of a guidewire is determined (e.g., detected and/or tracked). In at least one embodiment, the guidewire is a coronary guidewire 402 disposed in a vessel (e.g., vessel 202) of a patient. The position of guidewire 402, as shown in image 400, may be determined by guidewire localization module 102.

Additionally, a reference system 500 relative to the coronary guidewire 402 system 500 is determined as described above with respect to FIG. 5. The reference system 500 may be based on a reference point 502, such as a position of a catheter on guidewire 402, and the length of guidewire 402.

In step 708, the guidewire position, as determined in step 706, is associated with a cardiac phase. In other words, a time reference in the heart cycle of the patient is correlated with a present location of the guidewire 402. The reference system 500 determined in step 706 is also associated with the appropriate cardiac phase. In this way, a current location of guidewire 402 and a unique reference system 500 is associated with a cardiac phase. In at least one embodiment, the appropriate cardiac phase is determined based at least in part on information from heart cycle monitor 104.

Further, in step 710, locations of boundaries of a vessel are extracted. Since vessels expand and/or contract in relation to the heart cycle, current vessel boundary locations correspond to the current point in the heart cycle. In at least one embodiment, the locations of vessel boundaries 302a-d of vessel 202 are extracted (e.g., determined, derived, etc.) by guidewire localization module 102, segmentation module 106, and/or mapping module 110, as described above with respect to FIG. 3. The locations of vessel boundaries 302a-d may be extracted using any appropriate techniques and may, in some embodiments, be based on the detected contrast agent from step 704.

In the same or alternative embodiments, the locations of vessel boundaries 302a-d are determined within the framework of the appropriate reference system 500. In this way, the locations of vessel boundaries 302a-d are associated with a point (e.g., offset from the beginning) of the heart cycle. The locations, reference system, and offset may be stored (e.g., in memory 806 and/or storage 804 of computer 800 described below) for later use. In other words, a unique image (e.g., frame) is created that has the locations of vessel boundaries associated with a specific cardiac phase in a heart cycle.

Method steps 704-710 may be repeated as necessary. That is, a heart cycle may be divided into any number of portions (e.g., intervals) and an image containing the locations of vessel boundaries may be created for each cardiac phase. Further, though described herein is separate method steps 704-710, one of skill in the art would recognize that these steps may be performed in other orders and/or may be performed substantially simultaneously.

In step 712, a check is performed to determine if a contrast agent is present. Contrast agents may be detected by contrast detection module 108 as described above. If a contrast agent is detected, the method returns control to step 706 and a position of the guidewire 402 is determined. An exemplary method for detecting the presence of contrast agents is described in co-pending U.S. Patent Application No. 60/974,100, filed Sep. 21, 2007, entitled "Detection of Contrast Injection in 2D+time Fluoroscopic Volumes", the contents of which is incorporated herein by reference.

In step 714, the locations of the vessel boundaries 302a-d corresponding to the temporal reference point are imported to mapping module 110. That is, based on the cardiac phase information, the corresponding offset and vessel boundary locations determined in steps 708 and 710 are recalled. In this way, when no contrast agent is present, the locations of vessel boundaries may be looked up by mapping system 100. The vessel boundary locations corresponding to the appropriate cardiac phase are found and added to a non contrast-enhanced image in step 716.

In step 716, a non contrast-enhanced image (e.g., image 600) is modified based on the locations of the vessel boundaries 302a-d imported in step 714. That is, an image may be obtained in fluoroscopy after a contrast agent has been absorbed by the body and no longer provides contrast in the relevant vessels. It is advantageous to determine the vessel location without introducing further contrasting agent, which may harm a patient. Therefore, the image that is not contrast-enhanced is obtained using appropriate imaging techniques and is modified by inserting (e.g., overlaying, drawing in, etc.) the vessel boundary locations determined in step 710 that correspond to the same offset as the offset of the non contrast-enhanced image. In some embodiments, the non contrast-enhanced image is further modified by darkening the pixels of the image that fall between the vessel boundaries 302a-d.

FIG. 6 depicts such a modified non contrast-enhanced image. Image 600 is thus a contrast-free frame that has a "virtual map" of vessel 202 at a particular point in the heart cycle of the patient. Medical personnel may then use the virtual map of the vessel to proceed with any appropriate medical procedures while avoiding further, potentially harmful, use of contrast agents.

The method ends at step 718.

Figure 8:
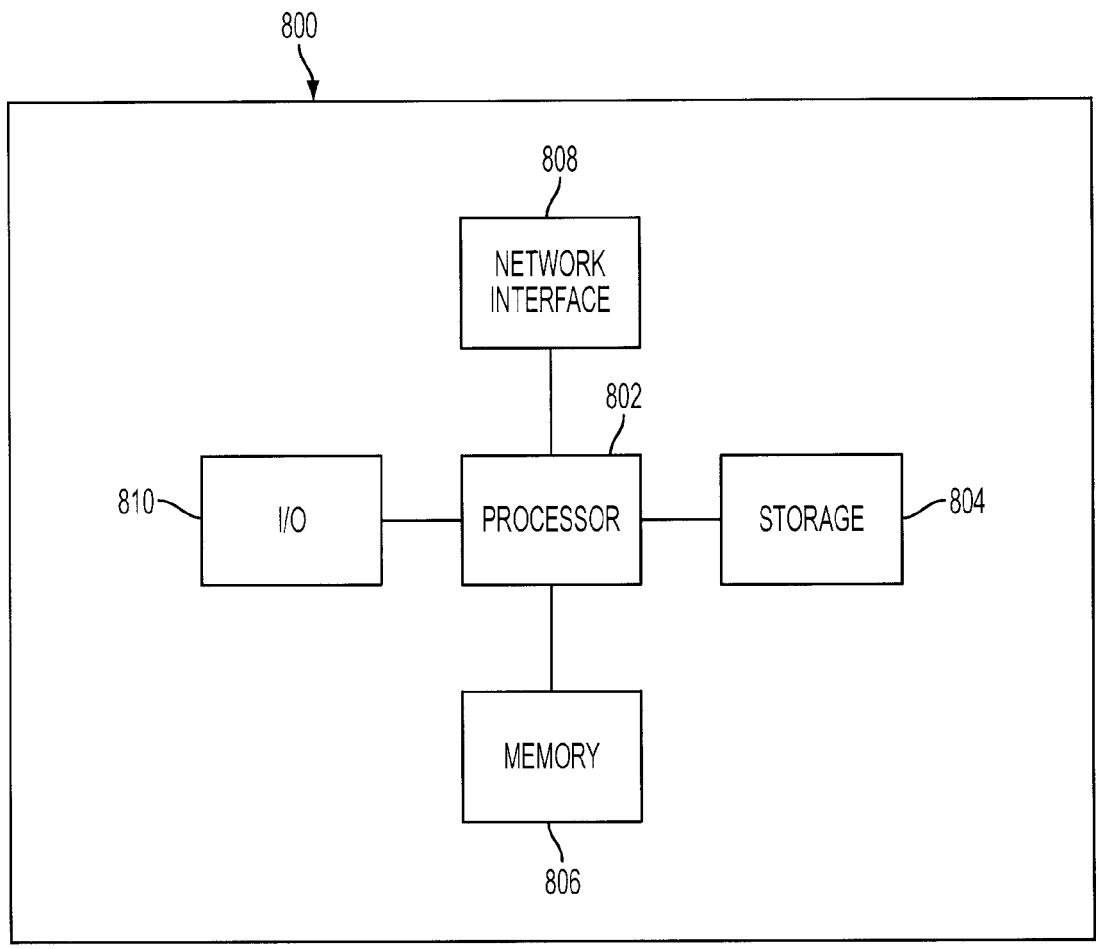
FIG. 8 is a schematic drawing of a computer.

FIG. 8 is a schematic drawing of a computer 800 according to an embodiment of the invention. Computer 800 may be used in conjunction with and/or may perform the functions of mapping system 100 and/or the method steps of method 700.

Computer 800 contains a processor 802 that controls the overall operation of the computer 800 by executing computer program instructions, which define such operation. The computer program instructions may be stored in a storage device 804 (e.g., magnetic disk, database, etc.) and loaded into memory 806 when execution of the computer program instructions is desired. Thus, applications for performing the herein-described method steps, such as guidewire localization, segmentation, mapping, etc., in method 700 are defined by the computer program instructions stored in the memory 806 and/or storage 804 and controlled by the processor 802 executing the computer program instructions. The computer 800 may also include one or more network interfaces 808 for communicating with other devices via a network. The computer 800 also includes input/output devices 810 (e.g., display, keyboard, mouse, speakers, buttons, etc.) that enable user interaction with the computer 800. Computer 800 and/or processor 802 may include one or more central processing units, read only memory (ROM) devices and/or random access memory (RAM) devices. One skilled in the art will recognize that an implementation of an actual controller could contain other components as well, and that the controller of FIG. 8 is a high-level representation of some of the components of such a controller for illustrative purposes.

According to some embodiments of the present invention, instructions of a program (e.g., controller software) may be read into memory 806, such as from a ROM device to a RAM device or from a LAN adapter to a RAM device. Execution of sequences of the instructions in the program may cause the computer 800 to perform one or more of the method steps described herein, such as those described above with respect to method 700. In alternative embodiments, hard-wired circuitry or integrated circuits may be used in place of, or in combination with, software instructions for implementation of the processes of the present invention. Thus, embodiments of the present invention are not limited to any specific combination of hardware, firmware, and/or software. The memory 806 may store the software for the computer 800, which may be adapted to execute the software program and thereby operate in accordance with the present invention and particularly in accordance with the methods described in detail above. However, it would be understood by one of ordinary skill in the art that the invention as described herein could be implemented in many different ways using a wide range of programming techniques as well as general purpose hardware sub-systems or dedicated controllers.

Such programs may be stored in a compressed, uncompiled, and/or encrypted format. The programs furthermore may include program elements that may be generally useful, such as an operating system, a database management system, and device drivers for allowing the controller to interface with computer peripheral devices, and other equipment/components. Appropriate general-purpose program elements are known to those skilled in the art, and need not be described in detail herein.

An exemplary method of mapping vessels according to an embodiment of the invention is described hereafter with particular attention to method 700 above as well as FIGS. 9-16 below. In such an embodiment, there are three stages of virtual coronary mapping. Stage 1 (analogous to method steps 704-708) detects the appearance and motion of a guidewire through fluoroscopic images acquired at different cardiac phases when no contrast agent is currently administrated to a patient. That is, a plurality of positions of a coronary guidewire in a plurality of non-contrast enhanced fluoroscopic images are determined. Stage 2 (analogous to method step 710) detects and segments a coronary vessel of interest during the administration of a contrast agent. The coronary vessel of interest is selected by using the shape of the guidewire from Stage 1. In other words, in a plurality of contrast enhanced fluoroscopic images, a plurality of reference points of a vessel segment corresponding to the plurality of positions of the coronary guidewire in a plurality of contrast enhanced fluoroscopic images are determined. Stage 3 (analogous to method steps 712-716) detects and tracks the current position of the guidewire after a contrast agent has dissipated, renders in real-time the contrast captured at Stage 2 and creates a "virtual contrast". In at least one embodiment, a non-contrast enhanced fluoroscopic image based at least in part on the determined plurality of reference points of a vessel segment is modified in Stage 3.

In Stage 1, a learning based guidewire detection in the first frame is performed using any appropriate method. In at least one embodiment, a user could hand edit the detection results. In another embodiment, learning-based guidewire detection in the first frame may be performed using the method described in Adrian, et. al "Hierarchical Learning of Curves Application to Guidewire Localization in Fluoroscopy," incorporated herein by reference.

The detection of the first frame is used as before, and robust tracking of guidewire shape across one heart cycle is performed. The tracking is decomposed into two stages. First, a global translational motion of the whole guidewire is estimated to compensate for the rigid component of guidewire motion, as shown in FIG. 9.

Figure 9:
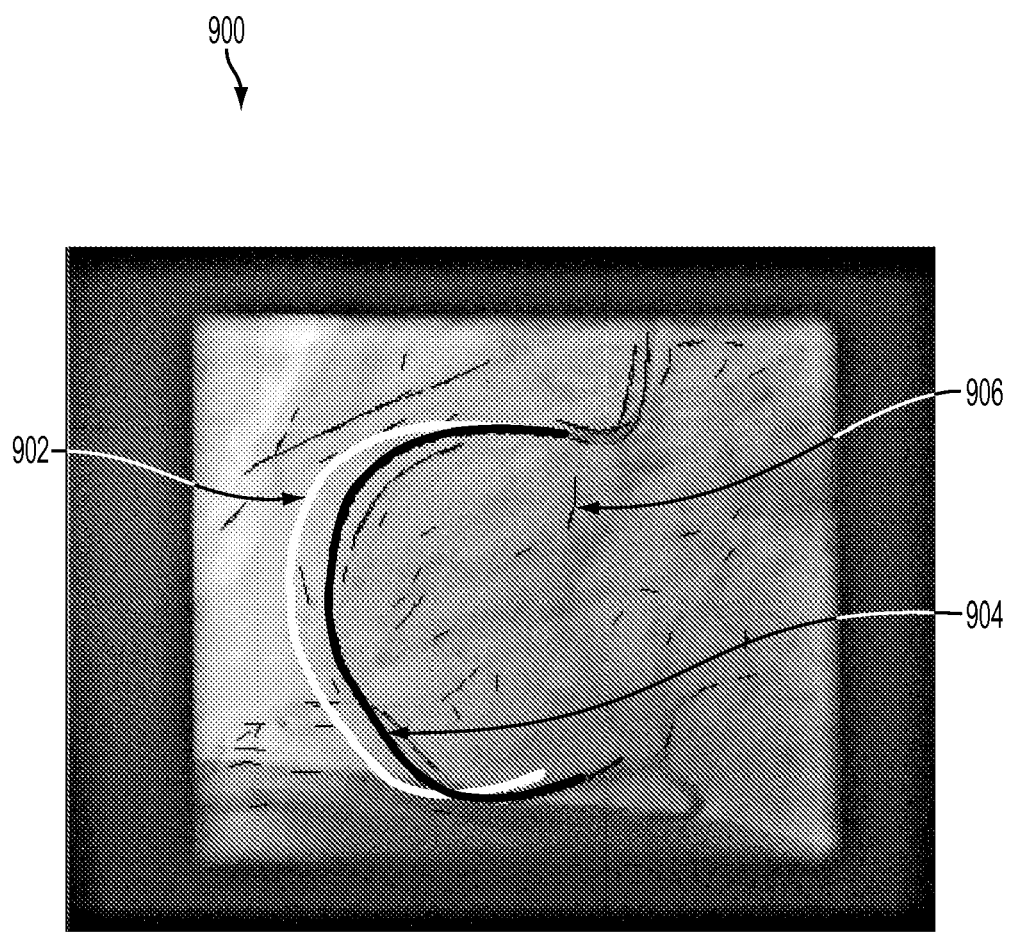
FIG. 9 depicts a representation of an image depicting estimation of a global translation.

FIG. 9 depicts a representation of an image 900 depicting estimation of a global translation. Image 900 may be obtained using mapping system 100 and is discussed in further detail below. Guidewire-like segments 902 may be obtained by applying a learning-based guidewire segment detection. One or more prior guidewire shapes 904 may be detected and tracked from a previous frame (e.g., image). Prior guidewire shapes 906 may be shifted by an estimated translation, as described in detail above with respect to method 700.

A kernel-based robust estimation is formulated as optimizing the following matching function between two feature sets $\{y_i\}$ and $\{z_j\}$. Accordingly, $$T_{opt} = \operatorname{argmax} \sum_i \sum_j \exp\left(\frac{1}{\sigma^2}\|y_i - (z_j + T)\|^2\right)$$

where $\{y_i\}$ is the set of 2D locations of guidewire-like segments 902 detected by the learning-based guidewire detector, $\{z_j\}$ is a set of 2D locations of points on the prior guidewire shape 904 detected in the first frame, T is a 2D translation vector, and exp(.) is an exponential function which defines a robust kernel with bandwidth $\sigma^2$.

Second, local deformation of each guidewire part is estimated to capture the non-rigid component of guidewire motion, using kernel based non-rigid motion estimation. For each frame to be processed, the guidewire shape in the previous frame will be used as before and the objective is to maximize the fitting score of the prior frame to the measurements in the current frame. The measurements are detected guidewire segments obtained using a learning based segment detector.

Figure 10A:
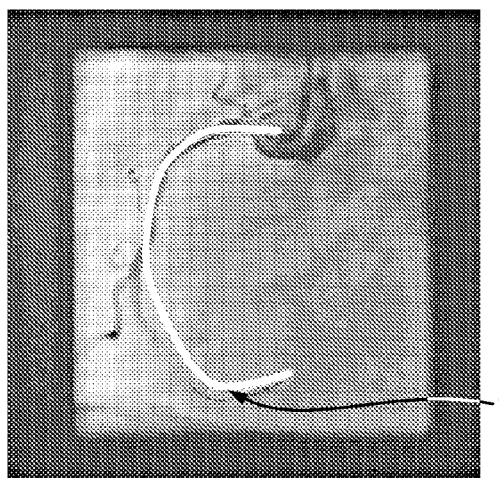
FIG. 10A depicts a representation of an image showing the tracking results of a guidewire before non-rigid deformation.
Figure 10B:
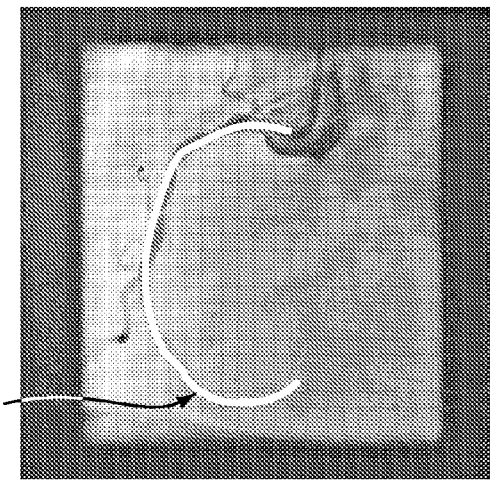
FIG. 10B depicts a representation of an image showing the tracking results of a guidewire after non-rigid deformation.

FIGS. 10A and 10B depict representations of an image 1000 showing the tracking results 1002 of a guidewire before non-rigid deformation and the tracking results 1004 of a guidewire after non-rigid deformation, respectively. Once the global translation is compensated, the non-rigid motion will be estimated non-parametrically. This may be accomplished using a multi-resolution framework. First, a large kernel size is used and kernel size is reduced in the subsequent iterations to construct density fields based on measurements (e.g., detected segments). The prior guidewire shape is represented using a spline. The control points of the spline will be moved in the direction perpendicular to the local spline direction to search for better fitting. The fitting score is defined as the sum of the score of all the points in the spline. The score of each point is the value of the density field in its location. The multi-resolution framework helps to accommodate large non-rigid motion and reduce the probability of falling into local maxima.

Figure 11:
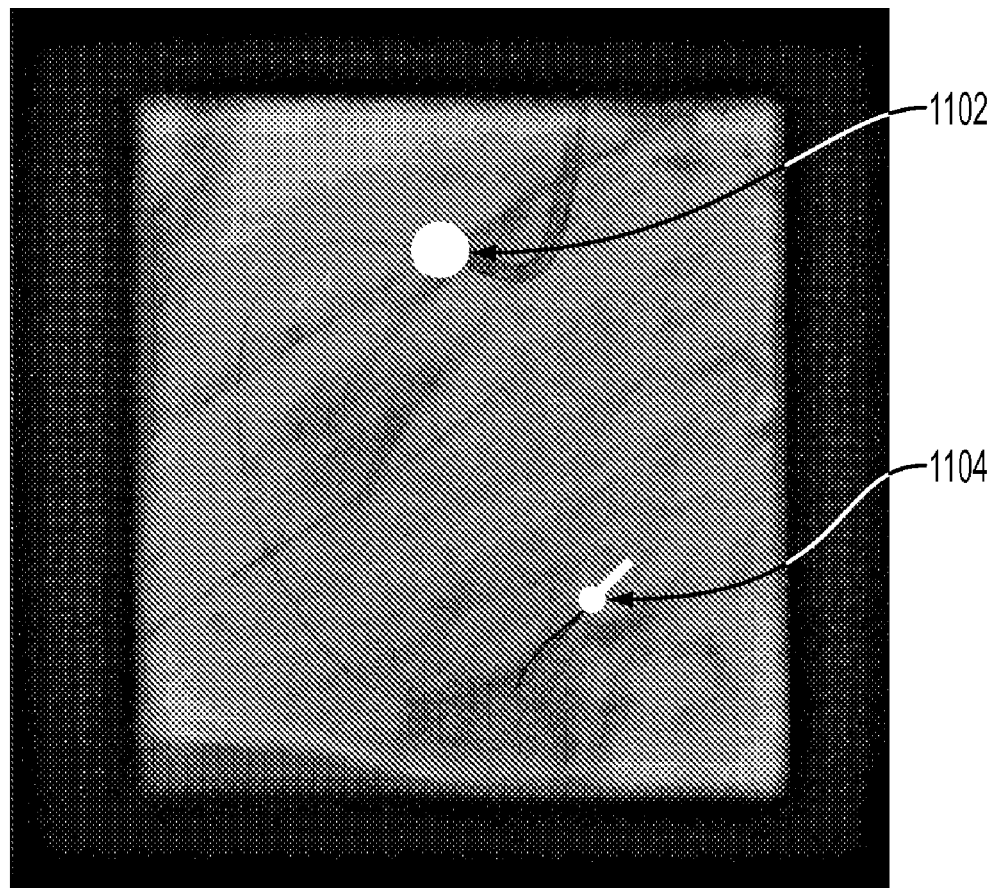
FIG. 11 depicts a representation of an image showing a guidewire with a detected catheter end and a detected guidewire tip.

Next, the location of the guidewire is refined by integrating the detection of guidewire tip and catheter end as shown in FIG. 11. FIG. 11 depicts a representation of an image 1100 showing a guidewire 1102 with a detected catheter end 1104 and a detected guidewire tip 1106. Such detection may use learning-based classifiers. The detected guidewire tip 1106 and detected catheter end 1104 define two end points of the guidewire 1102.

Figure 12:
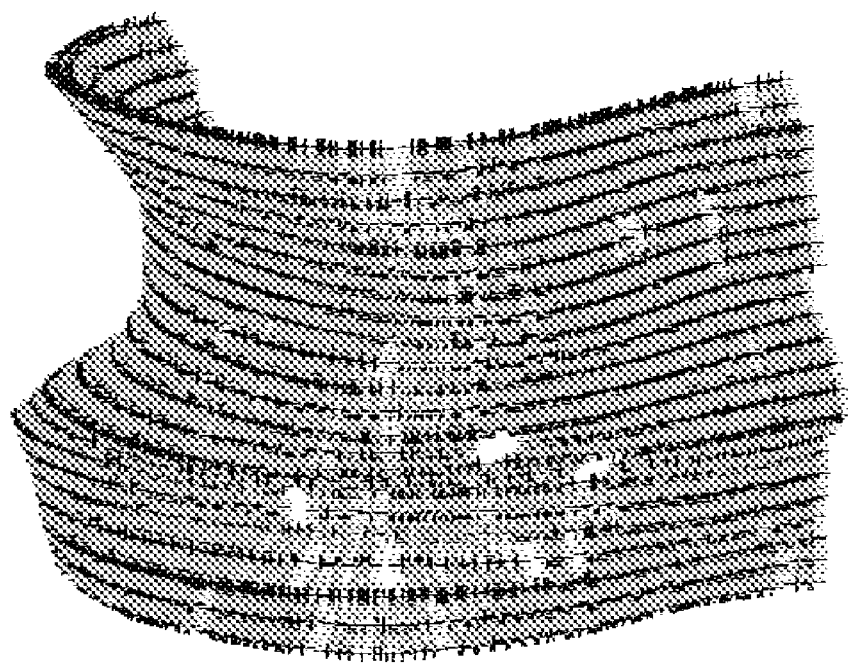
FIG. 12 depicts a representation of an image of an interpolated 3D surface.

Using the processing described above, a set of guidewire shapes represented as 2D curves may be obtained at various cardiac phases across a heart cycle. A 3D surface can be interpolated from the set of guidewire shapes using the medial axis between a pair of 2D curves. FIG. 12 depicts a representation of an image 1200 of an interpolated 3D surface.

In Stage 2, a coronary vessel is detected and tracked during administration of a contrast. Only one heart cycle with visible contrast is needed for processing. This cycle is called the contrast cycle. The detection and tracking of a coronary vessel is described below with respect to FIGS. 13-16.

Figure 13:
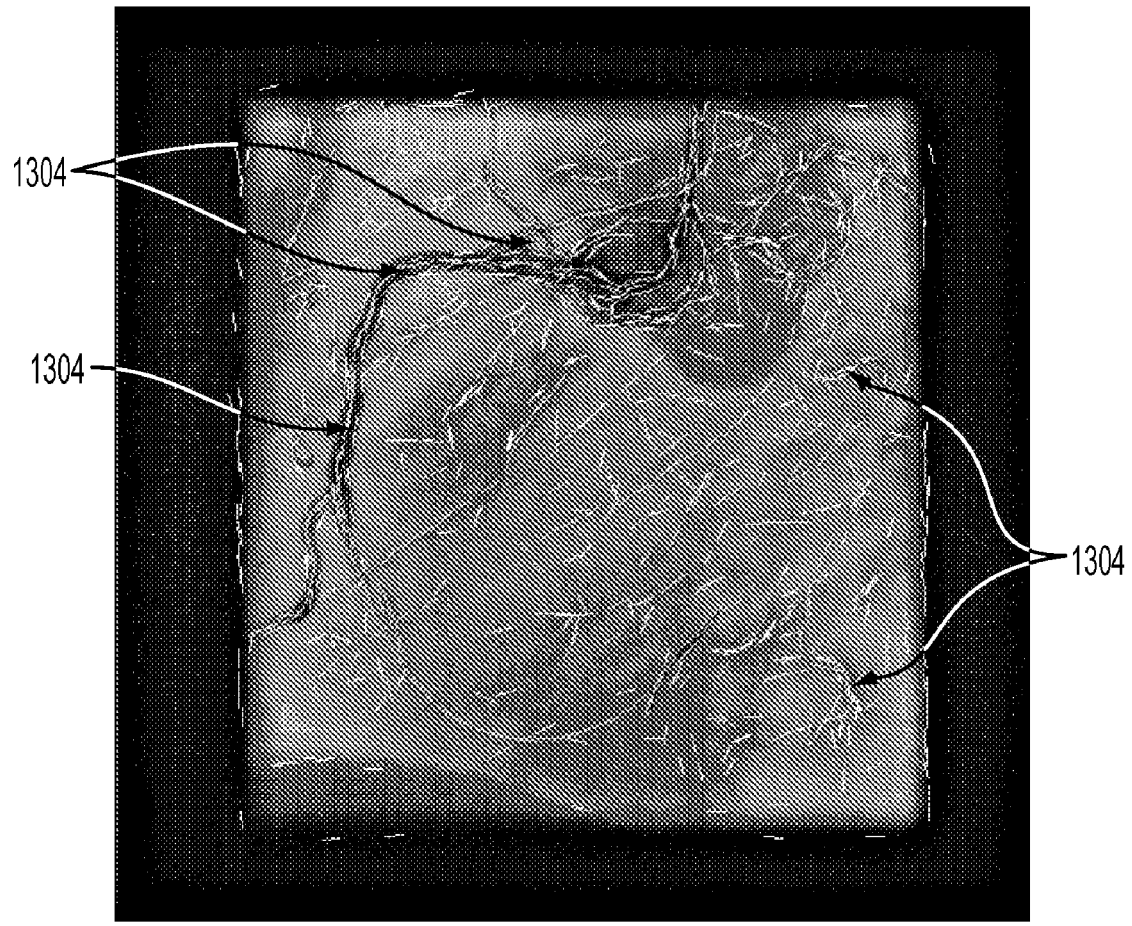
FIG. 13 depicts a representation of an image of detected vessel segments and guidewire segments.

First, the centerline of the vessel is inferred (e.g., determined, etc.) by applying learning-based detection of vessel cross segments. Vessel cross segments are rotated 90 degrees to obtain a set of vessel centerline segments. Those segments are combined with segments detected by a guidewire detector as measurements in tracking. FIG. 13 depicts a representation of an image 1300 of detected vessel segments 1302 and guidewire segments 1304.

Figure 14:
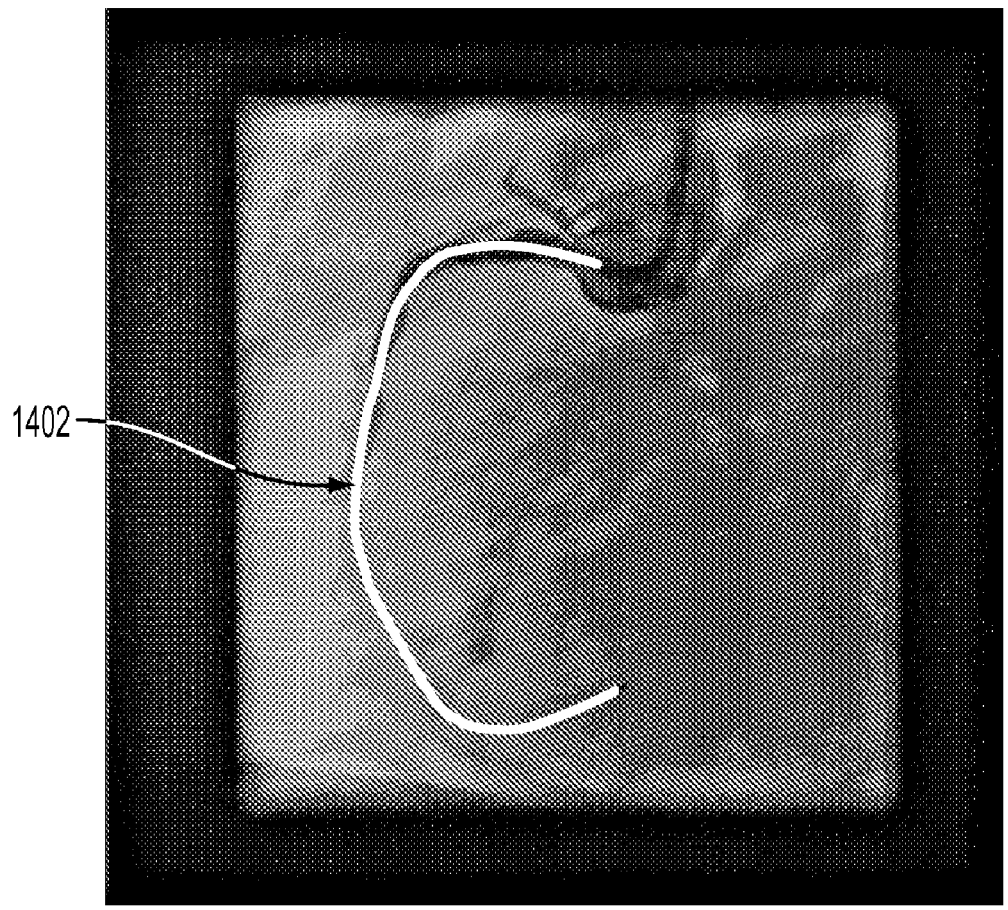
FIG. 14 depicts a representation of an image of an inferred vessel centerline.

Second, using the segments of all the frames in the whole cardiac cycle as measurements and the 3D surface interpolated from guidewire shapes in Stage 1 (e.g., image 1200) as before, the fitting probability is maximized to infer the centerline. The procedure is similar to the guidewire-tracking scheme described above with respect to Stage 1 and method steps 704-708. FIG. 14 depicts a representation of an image 1400 of an inferred vessel centerline 1402.

Figure 15:
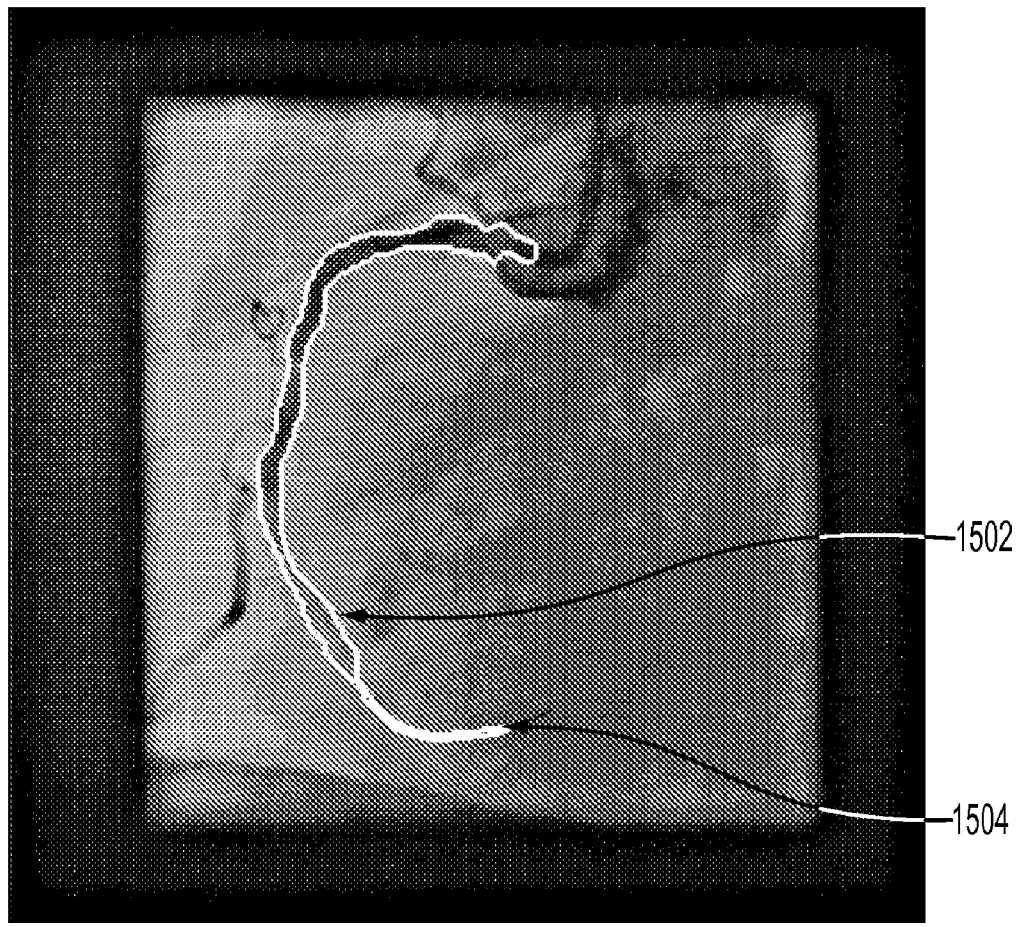
FIG. 15 depicts a representation of an image of a graph cut segmentation result.
Figure 16:
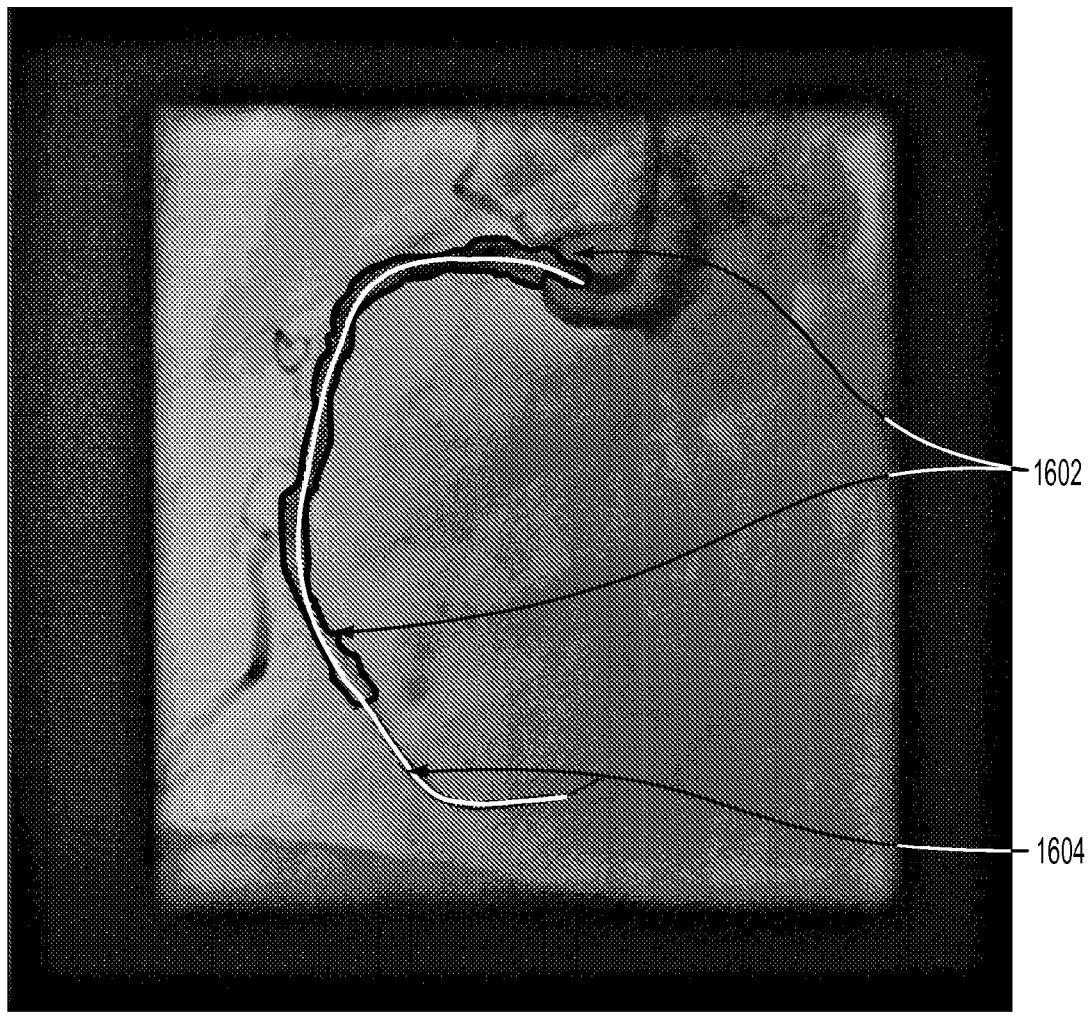
FIG. 16 depicts a representation of an image of a final resultant image depicting vessel boundaries as well as a guidewire.

Third, vessel boundaries are estimated as described above. In at least one embodiment a graph cut method, as is known, and a learning based vessel boundary detector are used to get a precise vessel boundary. Using the learning-based boundary detector, some false segmentation of a graph cut is removed. FIG. 15 depicts a representation of an image 1500 of a graph cut segmentation result 1502. FIG. 15 also show some false segmentation 1504 in the lower part because the contrast is weak in the image. As a result, some background is also included as vessel area. FIG. 16 depicts a representation of an image 1600 of a final result depicting vessel boundaries 1602 as well as the guidewire 1604.

In Stage 3, virtual maps of the vessels are created as new images (e.g., frames) when the contrast agent has dissipated. The locations of the determined vessel boundaries are imported to a mapping system and an image acquired without using a contrast agent is modified based on the imported locations of vessel boundaries. This creates a virtual map of the vessels.

Following the same procedure of guidewire tracking as described in Stage 1, the guidewire of each frame is located in Stage 3. For each frame in Stage 3, the corresponding contrast frame is acquired in the contrast cycle of Stage 2. The guidewire in the current frame and the centerline in the corresponding contrast frame are both one dimensional curves. Point to point correspondences along the two curves are set up according to their positions along the curve. Using a local relative coordinate system, such as the coordinate system described above with respect to FIG. 5, the intensity in the contrast frame is mapped to the current frame, thus generating the virtual contrast. In at least one embodiment, only the pixel inside the detected vessel boundary is mapped. In this way, a "virtual" map of the vessel is provided in an image that is not contrast-enhanced.

Of course, the various exemplary embodiments discussed above may be performed in a variety of manners in accordance with the system 100 and method 700 described above. For example, a position of a coronary guidewire may be determined in a first image by applying an image-based guidewire detector, an image-based guidewire tip detector, and an image-based catheter end detector. The image-based guidewire detector may be learned from a set of guidewire images using marginal space learning and a probabilistic boosting tree. The image-based guidewire tip detector may be learned from a set of guidewire tip images using a probabilistic boosting tree and steerable filters. The image-based catheter end detector may be learned from a set of catheter end images using a probabilistic boosting tree.

A position of a coronary guidewire may be determined by tracking a two-dimensional guidewire shape in subsequent images. A guidewire may be tracked by a first robust estimation of translational motion of a two-dimensional guidewire shape followed by a second robust estimation of non-rigid deformation of a two-dimensional guidewire shape. A first robust estimation of translational motion of a two-dimensional guidewire shape may be obtained by optimizing a kernel-based matching function between two sets of guidewire features where the guidewire features are obtained by applying an image-based guidewire detector. A second robust estimation of non-rigid deformation of a two-dimensional guidewire shape may be obtained by matching a guidewire shape with a previous vessel shape and by optimizing the probability of guide appearance where a previous vessel shape is obtained using the guidewire detected and tracked in a previous frame and a probability of a guidewire appearance is computed by applying an image-based guidewire detector. The guidewire shape may be further refined by integrating the results of guidewire tip detection and catheter end detection.

A centerline and the boundaries of a coronary vessel segment may be determined by applying an image-based vessel detector where the image-based vessel detector is learned from a set of vessel segment images using marginal space learning and probabilistic boosting tree and the boundaries of a coronary vessel are obtained using graph cuts and a learned vessel boundary detector. A centerline of a coronary vessel segment may be determined by tracking a two-dimensional vessel shape in subsequent images where a coronary vessel segment is tracked by a first robust estimation of translational motion of a two-dimensional vessel shape followed by a second robust estimation of non-rigid deformation of a two-dimensional vessel shape. A first robust estimation of translational motion of a two-dimensional vessel shape may be obtained by optimizing a kernel-based matching function between a set of vessel features and a set of guidewire features where the vessel features are obtained by applying an image-based vessel detector and the guidewire features are obtained by applying an image-based guidewire detector. A second robust estimation of non-rigid deformation of a two-dimensional vessel shape may be obtained by matching a vessel shape with a previous vessel shape and by optimizing the probability of vessel appearance where a previous vessel shape is obtained and the corresponding guidewire is detected and tracked in a previous frame, and the probability of a vessel appearance is computed by applying an image-based vessel detector. Further, a contrast free image may be modified by mapping the pixel intensities around a guidewire with the corresponding vessel in a contrast-injected image to the proximity of the guidewire in a contrast free image.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for mapping vessels comprising:
   determining a plurality of positions of a coronary guidewire in a plurality of non-contrast enhanced fluoroscopic images;
   determining, in a plurality of contrast enhanced fluoroscopic images, a plurality of reference points of a vessel segment corresponding to the plurality of positions of the coronary guidewire in a plurality of contrast enhanced fluoroscopic images; and
   modifying a non-contrast enhanced fluoroscopic image based at least in part on the determined plurality of reference points of a vessel segment.

2. The method of claim 1 further comprising:
   determining a reference system relative to the coronary guidewire;
   detecting a contrast agent contrasting the vessels; and
   extracting the locations of a plurality of vessel boundaries relative to the determined reference system based on the contrasted vessels.

3. The method of claim 2 wherein the reference system is a relative coordinate system wherein a first dimension of the relative coordinate system is a length along the coronary guidewire relative to a reference point and a second dimension of the relative coordinate system is a distance between the coronary guidewire and a vessel boundary.

4. The method of claim 3 wherein the reference point is a location of a catheter along the coronary guidewire.

5. The method of claim 1 further comprising:
   determining a position of a coronary guidewire in a first of the plurality of non-contrast enhanced fluoroscopic images by applying an image-based guidewire detector, and image-based guidewire tip detector, and an image-based catheter end detector.

6. The method of claim 5 further comprising:
   learning the image-based guidewire detector from a set of guidewire images using marginal space learning and a probabilistic boosting tree;
   learning the image-based guidewire tip detector from a set of guidewire tip images using a probabilistic boosting tree and steerable features; and
   learning the image-based catheter end detector from a set of catheter end images using a probabilistic boosting tree.

7. The method of claim 1 further comprising:
   determining a position of the coronary guidewire by tracking a two-dimensional guidewire shape in a plurality of images.

8. The method of claim 7 further comprising:
   tracking the coronary guidewire with a robust estimation of translational motion of a two-dimensional guidewire shape; and
   tracking the coronary guidewire with a robust estimation of non-rigid deformation of a two-dimensional guidewire shape.

9. The method of claim 8 wherein the position of the coronary guidewire is further refined by integrating results of a guidewire tip detection and a catheter end detection.

10. The method of claim 1 further comprising:
    determining a centerline and a plurality of vessel boundaries of a coronary vessel segment by applying an image-based vessel detector learned from a set of vessel segment images using marginal space learning and a probabilistic boosting tree.

11. The method of 10 further comprising:
    determining the plurality of vessel boundaries of the coronary vessel segment using graph cuts and a learned vessel boundary detector.

12. The method of claim 1 further comprising:
    modifying a contrast free image by mapping pixel intensities around a guidewire.

13. A method of coronary mapping:
    determining a position of a coronary guidewire in a coronary vessel segment;
    determining a centerline of the coronary vessel segment; and
    determining a plurality of boundaries of the coronary vessel segment;
    wherein determining a position of a coronary guidewire comprises:
       determining an estimation of translational motion of a two-dimensional coronary guidewire shape; and
       determining an estimation of non-rigid deformation of the two-dimensional guidewire shape;
    wherein determining an estimation of translational motion of a two-dimensional guidewire shape comprises:
       determining a first set of guidewire features using an image-based guidewire detector;
       determining a second set of guidewire features using an image-based guidewire detector; and
       optimizing a kernel-based matching function between the first set of guidewire features and the second set of guidewire features.

14. The method of claim 13 wherein optimizing a kernel-based matching function between the first set of guidewire features and the second set of guidewire features comprises determining $$T_{opt} = \text{argmax} \sum_i \sum_j \exp\left(\frac{1}{\sigma^2} \|y_i - (z_j + T)\|^2\right)$$

wherein $\{y_i\}$ is the first set of guidewire features, $\{z_i\}$ is the second set of guidewire features, T is a two-dimensional translation vector, and $$\exp\left(\frac{1}{\sigma^2} \|y_i - (z_j + T)\|^2\right)$$

is an exponential function that defines a robust kernel with a bandwidth of hu 2.

15. The method of claim 13 wherein determining an estimation of non-rigid deformation of the two-dimensional coronary guidewire shape comprises:
   determining a vessel shape;
   matching the two-dimensional coronary guidewire shape with the vessel shape; and
   optimizing a probability of a vessel appearance with an image-based vessel detector.

16. The method of claim 15 wherein determining a vessel shape comprises:
   detecting a location of the coronary guidewire in an image frame; and
   tracking the coronary guidewire in the image frame.

17. The method of claim 13 wherein determining a centerline of the coronary vessel segment comprises:
   determining a two-dimensional vessel shape in a plurality of image frames;
   determining a estimation of translational motion of the two-dimensional shape; and
   determining an estimation of non-rigid deformation of the two-dimensional vessel shape.

* * * * *